US00PP21064P2

(12) United States Plant Patent
Walvatne

(10) Patent No.: US PP21,064 P2
(45) Date of Patent: Jun. 15, 2010

(54) ***COTINUS* PLANT NAMED 'NORTHSTAR'**

(50) Latin Name: *Cotinus obovatus*
Varietal Denomination: Northstar

(76) Inventor: Bradley C. Walvatne, 28325 Hwy 145, Battle Lake, MN (US) 56515

( * ) Notice: Subject to any disclaimer, the term of this patent is extended or adjusted under 35 U.S.C. 154(b) by 0 days.

(21) Appl. No.: 12/380,119

(22) Filed: Feb. 24, 2009

(51) Int. Cl.
*A01H 5/00* (2006.01)

(52) U.S. Cl. ..... Plt./226
(58) Field of Classification Search ..... Plt./226, Plt./216
See application file for complete search history.

*Primary Examiner*—June Hwu
(74) *Attorney, Agent, or Firm*—Penny J. Aguirre

(57) ABSTRACT

A new cultivar of *Cotinus obovatus*, 'Northstar', characterized by its cold hardiness in U.S.D.A. Zone 3, its heavy bloom of pink inflorescences in mid summer, its red and orange fall foliage color, its drought tolerance once established, and its adaptability for growth in poor soils, a wide range of soil pH, and partial sun.

2 Drawing Sheets

Botanical classification: *Cotinus obovatus*.
Variety denomination: 'Northstar'.

BACKGROUND OF THE INVENTION

The present invention relates to a new and distinct cultivar of American smoketree, botanically known as *Cotinus obovatus* 'Northstar' and will be referred to hereafter by its cultivar name, 'Northstar'.

The Inventor discovered 'Northstar' as a naturally occurring whole plant mutation of *Cotinus obovatus* in summer of 1996 in a residential garden in Star Lake, Ottertail County, Minn. The parentage of 'Northstar' is unknown as it is presumed to be a seedling of unnamed selections of *Cotinus obovatus*.

Asexual reproduction of the new cultivar was first accomplished by softwood cuttings in Battle Lake, Minn. in 1997. The characteristics of this cultivar have been determined by cuttings and in vitro propagation to be stable and are reproduced true to type in successive generations.

SUMMARY OF THE INVENTION

The following traits have been repeatedly observed and represent the characteristics of the new cultivar as observed for a period of twelve years and on propagated plants up to 10 years in age. These attributes in combination distinguish 'Northstar' as a unique cultivar of *Cotinus*.

1. 'Northstar' is cold hardy to U.S.D.A Zone 3 and withstood and thrived after a winter that was reported to have a low temperature of −51° F., a condition that killed all other known plants of *Cotinus obovatus* growing in the area that were known to the Inventor.
2. 'Northstar' produces a heavy production of showy pink inflorescences from mid June to mid July in Minnesota.
3. 'Northstar' is drought tolerant once established and is adaptable to growth in poor soils, a wide range to pH levels, and partial shade.
4. 'Northstar' has foliage that turns brilliant red and orange in fall.

'Northstar' as a unique and unlike any existing cultivars of *Cotinus obovatus* known to the inventor. 'Northstar' differs from *Cotinus obovatus* primarily in its cold hardiness, as plants of *Cotinus obovatus* are typically dependably cold hardy to U.S.D.A. Zone 5 and the species has a native range in U.S.D.A. Zones 5 to 8. 'Northstar' also has heavier blooming than is typical for selections of *Cotinus obovatus* as it produces a mass of pink clusters that are more typically observed with selections of *Cotinus coggygria*. The only cultivar of *Cotinus obovatus* known to the inventor is 'Red Leaf' (not patented), which is known for its deep red fall color but lacks the cold hardiness of 'Northstar'.

BRIEF DESCRIPTION OF THE DRAWING

The accompanying colored photographs illustrate the overall appearance and distinct characteristics of the new *Cotinus* as grown in Ottertail County, Minn.

The photograph in FIG. 1 and FIG. 2 were taken in mid summer of the original discovered plant of 'Northstar' (about 15 years in age).

Figure 1:
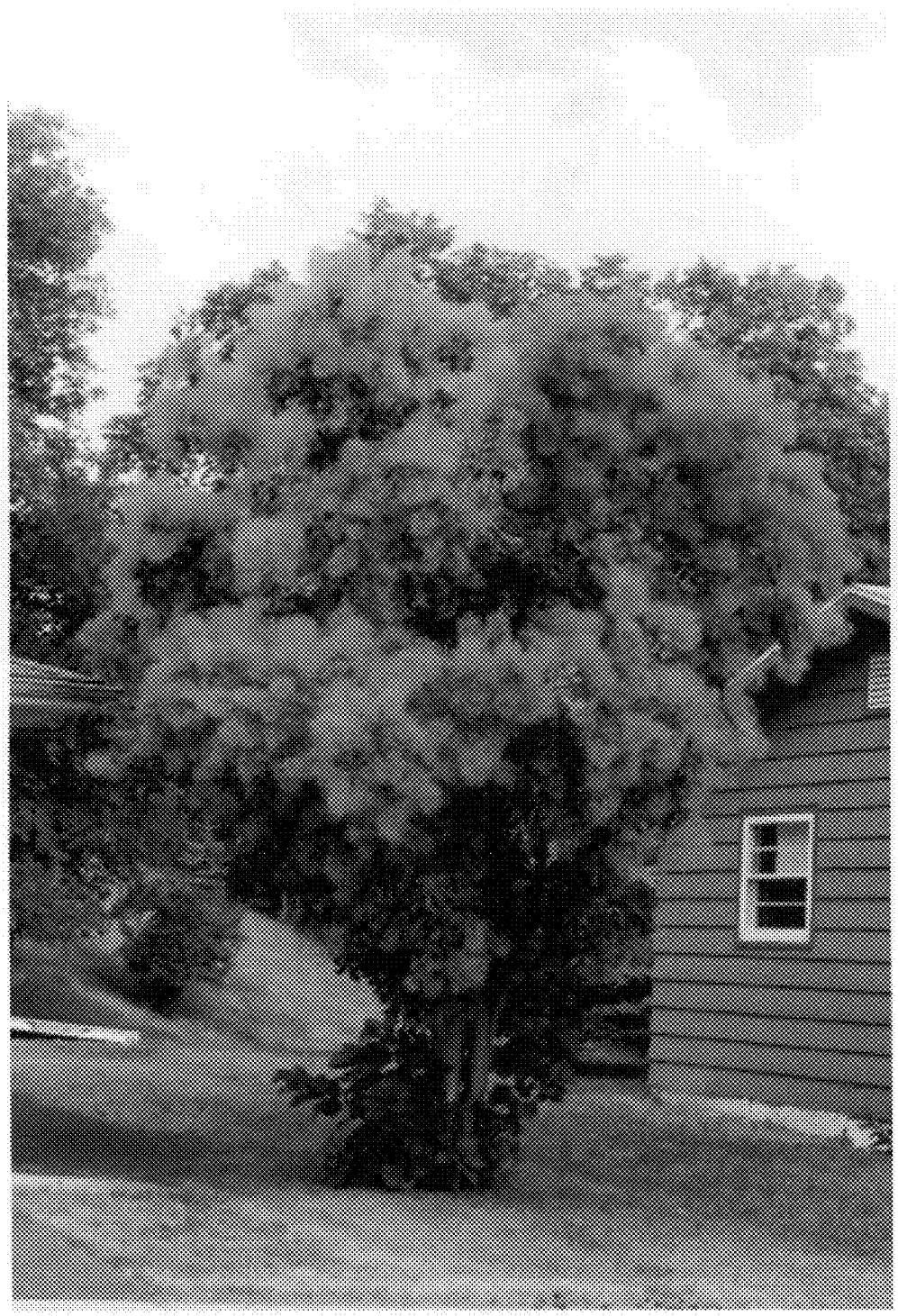
FIG. 1 provides a view of the plant habit in full bloom and the photograph in FIG. 2 provides a close-up of an inflorescence.
Figure 2:
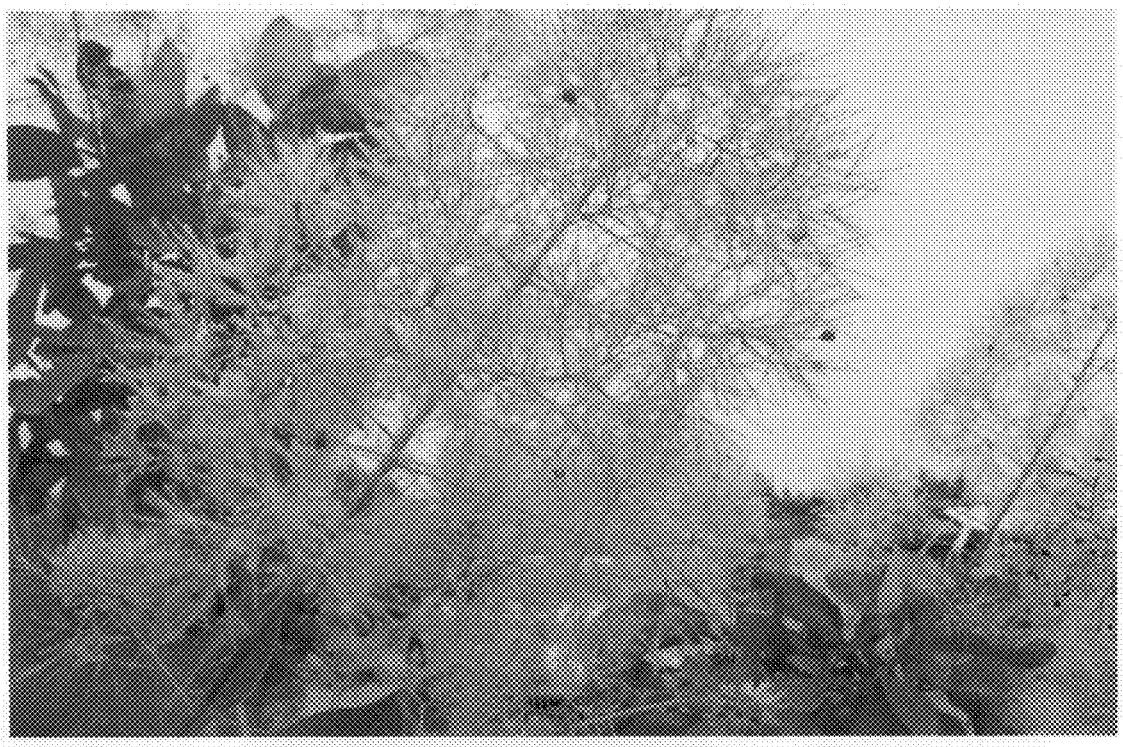
Figure 3:
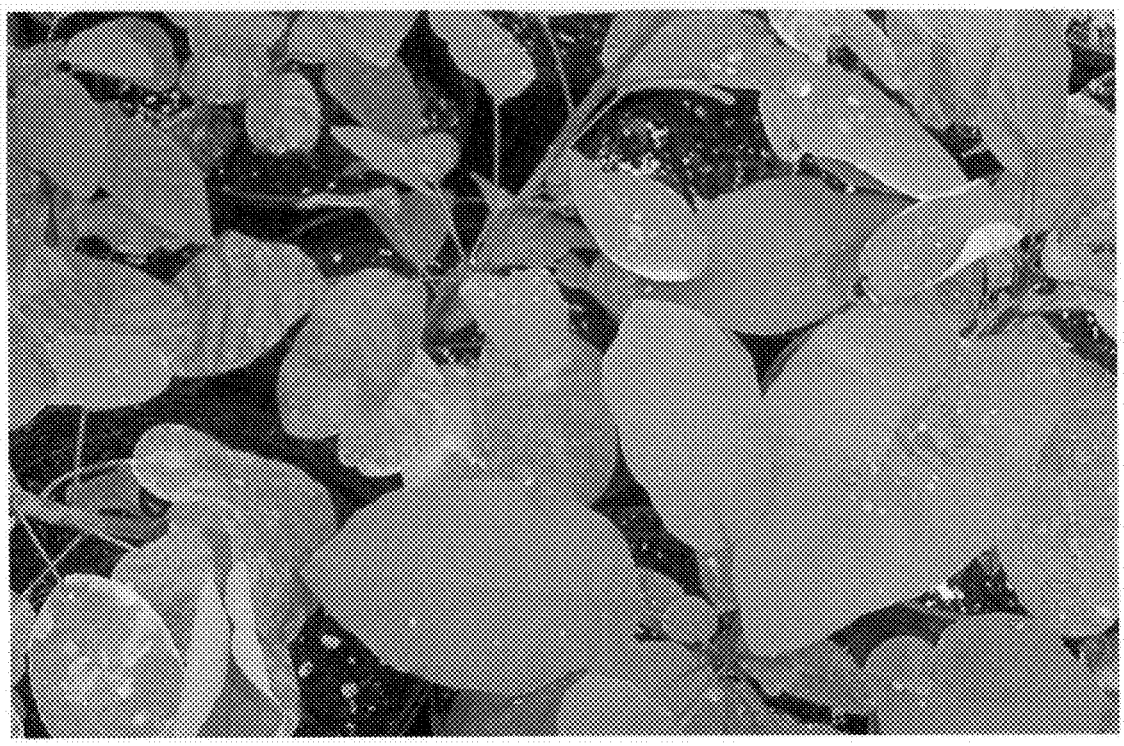

The photograph in FIG. 3 was taken in November of one year-old plants of 'Northstar' as grown in one-gallon containers and illustrates its fall foliage coloration.

The colors in the photographs may differ slightly from the color values cited in the detailed botanical description, which accurately describe the colors of the new *Cotinus*.

DETAILED BOTANICAL DESCRIPTION

The following is a description of the new cultivar as observed for 12 years on the original tree with the detailed botanical data taken from a 4 year-old plant as grown in a 5-gallon container outdoors in a nursery in Battle Lake, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Small flowers are present in May with the inflorescences becoming showy as the pedicels become villose from mid June to mid July.

*Plant habit.*—Broadly upright.

*Height and spread.*—Mature trees reaches about 18 to 25 feet in height and about 12 to 20 feet in width, plants 4 years in age reach about 58 inches in height and 44 inches in width.

*Cold Hardiness.*—U.S.D.A. Zone 3.

*Diseases and pests.*—No disease or pest problems have been observed.

*Culture.*—Grows best in full sun but is tolerant to partial shade, drought tolerant once established and is adaptable to growth in poor soils and a wide range to pH levels.

*Root description.*—Fibrous.

Growth and propagation:

*Propagation.*—Softwood cuttings and tissue culture (preferred).

*Growth rate.*—Vigorous.

Stem description:

*Shape.*—Oval.

*Branching.*—Multi-stemmed, well-branched in irregular pattern most typically loosely alternate or whorled (especially if pinched).

*Stem color.*—Young twigs; a blend of N199B and 148A with vertical lenticels 161B (about 12 per square cm), other branches (bark); a blend of 199D, 201B and 201C with fissures and horizontal lenticels 199A (about 15 per square cm).

*Stem size* (4 *year-old tree*).—Main stem averages 3.4 cm in width as measured 8 cm from base, lateral branches (emerge about 10 cm from base) average 65 cm in height and 1.2 cm in width, with secondary and tertiary branches (twigs) an average of 25 cm in length and 4 mm in width.

*Stem surface.*—Main stem and secondary branches are finely barked with horizontal lenticels twigs are smooth and semi-glossy with lenticels.

*Internode length.*—Highly variable and often whorled.

Foliage description:

*Leaf shape.*—Primarily broadly elliptic.

*Leaf division.*—Simple.

*Leaf base.*—Rounded.

*Leaf apex.*—Broadly acute.

*Leaf fragrance.*—None.

*Leaf venation.*—Pinnate, conspicuous, midrib 161A with a flush of 174A near base and lateral veins 145C in color on upper surface and midrib 160C with lateral veins 138C in color on lower surface.

*Leaf margins.*—Entire with very slight undulations.

*Leaf arrangement.*—Spiral to alternate.

*Leaf attachment.*—Petiolate.

*Leaf surface.*—Dull and glabrous on upper surface and dull, puberulent and very sparsely covered with longer hairs on lower surface.

*Leaf size.*—Variable and up to 12 cm in length and 8 cm in width when mature.

*Leaf quantity.*—About 17 on a branch 26 cm in length.

*Internode length.*—Irregular, 2 to 5 cm with longer lengths near base of branch.

*Leaf color.*—Summer; 137B to N137A on upper surface and a color between 138B and 191A to 191A on lower surface with newly emerging leaves flushed with N77C, fall; changes to a blend of N77C, 63B, 63C, and 14B.

*Petioles.*—Average of 2.6 cm in length and 2 mm in width, 161A in color with a flush of 174A on upper surface and 144B to 160C in color on lower surface, glabrous surface.

*Stipules.*—Absent.

Inflorescence description:

*Inflorescence type.*—Thyrse compound open pyramidal-shaped panicles on terminals of lateral branches and twigs, flowers are small and non-showy with the pedicels expanding and becoming plumose-villose and showy in mid summer.

*Inflorescence size.*—Average of 25 cm in length and 23 cm in width when showy.

*Rachis.*—Nearly quadrangular in shape, average of 19 cm in length and 2 mm in width with secondary branches an average of 6 cm in length and 1.2 mm in width, surface is glabrous, average internode length for secondary branches 2 cm, tertiary branches average 1.5 cm in length and 0.7 mm in width with an internode length of about 1 cm, 144B in color.

*Pedicels.*—About 5 mm in length and 0.4 mm in width, 144B in color, somewhat villose surface, after bloom; expand to 2.5 cm in length and 0.4 mm in width and very villose with hairs about 0.5 mm in length, 37C in color and hairs 37A in color, overall color is 37B to 37C, persistent and fading to 164B in color in fall, about 1,000 per inflorescence and not all pedicels produces flowers and/or fruit.

*Flower buds.*—Obovate in shape, 3 mm in depth and 2 mm diameter, 150B in color with sepal portion 144B in color.

*Flower fragrance.*—None.

*Lastingness of flowers.*—True flowers are short lived (less than one week) with showy pedicels lasting about one month with good color and fading in color but persisting into fall.

*Flower quantity.*—About 400 per compound inflorescence.

*Flower type.*—Star-shaped, rotate.

*Flower aspect.*—Upright on pedicels.

*Flower size.*—About 5 mm in diameter and 4 mm in depth.

*Petals.*—5, about 2 mm in length and 1.5 mm in width, un-fused and spreading, ovate in shape, truncate base, acute apex, glabrous surface, 150B in color.

*Sepals.*—5, about 1.7 mm in length and 1 mm in width, fused at base, acute apex, pubescent surface, 144B in color.

Reproductive organs:

*Pistils.*—1, filaments; 1.5 mm in length, stigma; club-shaped and 144C in color on very short style, ovary; superior; about 4 mm in length and width, 3-carpelled, 144A in color.

*Stamens.*—Not observed, plants of *Cotinus obovatus* are typically dioecious to polygamo-dioecious therefore stamen may be produced but were not observed on the plants available for data collection.

*Fruit and seed.*—Fruit; a compressed drupe, an average of 4 mm in length and width, about 100 per inflorescence, 144A in color, seed; 1, about 2 mm in length and width, obovate and flattened, 200B in color.

It is claimed:

1. A new and distinct cultivar of *Cotinus* plant named 'Northstar' as herein illustrated and described.

* * * * *